US010888605B2

(12) United States Patent
Moeller et al.

(10) Patent No.: US 10,888,605 B2
(45) Date of Patent: Jan. 12, 2021

(54) GLP-1 COMPOSITIONS AND USES THEREOF

(71) Applicant: Novo Nordisk A/S, Bagsvaerd (DK)

(72) Inventors: Eva Horn Moeller, Alleroed (DK); Michael Duelund Soerensen, Soeborg (DK); Joakim Lundqvist, Malmoe (SE)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/774,666

(22) Filed: Jan. 28, 2020

(65) Prior Publication Data

US 2020/0164042 A1    May 28, 2020

Related U.S. Application Data

(63) Continuation of application No. PCT/EP2018/072835, filed on Aug. 24, 2018.

(30) Foreign Application Priority Data

Aug. 24, 2017 (EP) ..................... 17187676

(51) Int. Cl.
| | | |
|---|---|---|
| *A61K 38/26* | (2006.01) | |
| *A61K 9/00* | (2006.01) | |
| *A61K 9/08* | (2006.01) | |
| *A61K 47/02* | (2006.01) | |
| *A61K 47/10* | (2017.01) | |

(52) U.S. Cl.
CPC ............ *A61K 38/26* (2013.01); *A61K 9/0019* (2013.01); *A61K 9/08* (2013.01); *A61K 47/02* (2013.01); *A61K 47/10* (2013.01)

(58) Field of Classification Search
CPC ...... A61K 38/26; A61K 9/0019; A61K 47/10; A61K 9/08; A61K 47/02
See application file for complete search history.

(56) References Cited

U.S. PATENT DOCUMENTS

| 5,169,771 | A | 12/1992 | Christner et al. |
|---|---|---|---|
| 9,764,003 | B2 | 9/2017 | Jensen |
| 2006/0178304 | A1 | 8/2006 | Juul-Mortensen et al. |
| 2009/0156478 | A1* | 6/2009 | Lau ................ A61P 3/10 514/1.1 |
| 2012/0208755 | A1 | 8/2012 | Leung |
| 2016/0235855 | A1 | 8/2016 | Xiong et al. |

FOREIGN PATENT DOCUMENTS

| JP | 2015522573 A | 8/2015 |
|---|---|---|
| WO | 9010020 A1 | 9/1990 |
| WO | 9217482 A1 | 10/1992 |
| WO | 9824767 A1 | 6/1998 |
| WO | 0069413 A1 | 11/2000 |
| WO | 0101774 A1 | 1/2001 |
| WO | 0102369 A2 | 1/2001 |
| WO | 2005042488 | 5/2005 |
| WO | 2005044294 | 5/2005 |
| WO | 2005081711 | 9/2005 |
| WO | 2006055603 | 5/2006 |
| WO | 2006072065 | 7/2006 |
| WO | 2006/097537 A2 | 9/2006 |
| WO | 2006096461 | 9/2006 |
| WO | 2006099561 | 9/2006 |
| WO | 2007075720 | 7/2007 |
| WO | 2007094893 | 8/2007 |
| WO | 2008019115 | 2/2008 |
| WO | 2009051992 | 4/2009 |
| WO | 2011069629 | 6/2011 |
| WO | 2012107476 A1 | 8/2012 |
| WO | 2012151248 | 11/2012 |
| WO | 2013072406 | 5/2013 |
| WO | 2013151663 | 10/2013 |
| WO | 2013151668 | 10/2013 |
| WO | 2013190384 | 12/2013 |
| WO | 2014060472 A1 | 4/2014 |
| WO | 2014182950 | 11/2014 |
| WO | 2015009616 | 1/2015 |
| WO | 2016001862 | 1/2016 |

OTHER PUBLICATIONS

BASF: "BASF Chemical Emergency Medical Guidelines," Jan. 1, 2016, Retrieved from the Internet: URL: https://www.basf.com/documents/corp/en/sustainability/employees-and-society/employees/occupational-medicine/medical-guidelines/Phenol_B_BASF_medGuidelines_E104.pdf , retrieved on Nov. 20, 2017.

Lau et al., Journal of Medicinal Chemistry, 2015, vol. 58, No. 18, pp. 7370-7380.

Marbury et al., "Pharmacokinetics and Tolerability of a Single Dose of Semaglutide, a Once-Weekly Human GLP-1 Analogue, in Subjects With and Without Renal Impairment," Diabetologia, 2014, vol. 57, Supplement: 1, pp. S358-S359.

* cited by examiner

*Primary Examiner* — Sudhakar Katakam
(74) *Attorney, Agent, or Firm* — Rosemarie R. Wilk-Orescan

(57) ABSTRACT

The present invention relates to pharmaceutical compositions of the GLP-1 peptide semaglutide comprising no more than 0.01% (w/w) phenol, their preparation, kits comprising such compositions as well as uses thereof.

14 Claims, No Drawings

GLP-1 COMPOSITIONS AND USES THEREOF

CROSS-REFERENCE TO RELATED APPLICATIONS

This application is a continuation of International Application PCT/EP2018/072835 (WO/2019/038412), filed Aug. 24, 2018, which claims priority to European Patent Application 17187676.6, filed Aug. 24, 2017; the contents of which are incorporated herein by reference.

The present invention relates to the field of pharmaceutical compositions comprising the GLP-1 peptide semaglutide.

BACKGROUND

GLP-1 peptides are known to be prone to develop lack of stability in liquid solutions, for example lack of physical stability. Thus, liquid pharmaceutical compositions comprising GLP-1 peptides with even better stability are desired. Such improved stability may be physical stability and/or chemical stability.

SUMMARY

In some embodiments the invention relates to liquid pharmaceutical compositions comprising semaglutide and no more than 0.01% (w/w) phenol. In some embodiments the invention relates to kits comprising the pharmaceutical composition as defined herein. In some embodiments the invention relates to the pharmaceutical composition as defined herein for use in medicine.

DESCRIPTION

The present invention relates to liquid pharmaceutical compositions comprising the GLP-1 peptide semaglutide and no more than 0.01% (w/w) phenol. Surprisingly, the present inventors found that such compositions have improved chemical and/or physical stability. In some embodiments the composition comprises no phenol. In some embodiments the composition comprises 0.01-10 mg/ml semaglutide. In some embodiments the composition has a pH in the range of 6.0-10.0, such as pH 7.0-7.8.

In some embodiments the composition of the invention is a liquid pharmaceutical composition comprising semaglutide and no more than 0.01% (w/w) phenol, wherein said composition
  a. is for parenteral administration;
  b. is an aqueous solution comprising at least 60% w/w water; or
  c. further comprises one or more pharmaceutically acceptable excipients selected from the group consisting of a buffer or an isotonic agent.

In some embodiments the composition of the invention is a liquid pharmaceutical composition comprising semaglutide, no more than 0.01% (w/w) phenol, and optionally one or more pharmaceutically acceptable excipients, wherein the formulation is for parenteral administration, such as subcutaneous administration.

In some embodiments the composition of the invention is a liquid pharmaceutical composition comprising semaglutide, no more than 0.01% (w/w) phenol, at least 60% w/w water, and optionally one or more pharmaceutically acceptable excipients.

In some embodiments the term "stability" as used herein refers to stability of semaglutide in a liquid pharmaceutical composition. In some embodiments stability is chemical stability of the GLP-1 peptide (e.g. determined by HPLC, such as Assay (I) herein), and optionally physical stability of the GLP-1 peptide (e.g. determined by Thioflavine T assay, such as Assay (II) herein).

In some embodiments the term "chemical stability" in relation to semaglutide as used herein refers to the covalent bonds of the semaglutide compound being substantially intact. In some embodiments chemical stability of a GLP-1 peptide is determined by HPLC, such as Assay (I) herein. In some embodiments a composition possess chemical stability if its covalent bonds are intact in at least 80% (w/v) of said GLP-1 peptides after storage for 3 months at 25° C. In some embodiments chemical stability of semaglutide is determined by Assay (IV) herein.

In some embodiments the term "physical stability" in relation to semaglutide as used herein refers to semaglutide forming substantially no aggregates, e.g. in the form of fibril formation. In some embodiments physical stability is determined by Thioflavine T assay, such as Assay (II) herein.

In some embodiments the composition of the present invention is a stable pharmaceutical composition. The term "stable pharmaceutical composition" when used herein refers to a pharmaceutical composition, e.g. a solution or suspension, comprising GLP-1 peptide, and which composition following storage comprises at least 80% (w/v) of said GLP-1 peptide (e.g. after quiescent storage for 3 months at 25° C.). Storage conditions for stability testing may be 2-8° C., such as 5° C., or at least 2.5 years at 5° C. Alternatively, storage conditions for stability testing may be at least 4 weeks, such as 6 weeks or 3 months, optionally at 30° C. The conditions of storage for this stable pharmaceutical composition may be at 5° C. for 1 or 2 years. The conditions of storage for this stable pharmaceutical composition may be at 5° C. for 3 years. Alternatively, the conditions of this storage may be at 25° C. for 24 hours or 1 week. In yet another alternative, the conditions of this storage may be room temperature for two months, such as up to two months.

In some embodiments, chemical stability of the GLP-1 peptide requires at least 80% (w/v), such as at least 90% (w/v) or at least 95% (w/v), of said GLP-1 peptide remaining with its covalent bonds intact at the end of the storage period. In some embodiments chemical stability of the GLP-1 peptide requires at least 95% (w/v), such as at least 97% (w/v) or at least 99% (w/v), of said GLP-1 peptide remaining with its covalent bonds intact at the end of the storage period.

The composition of the invention comprises no more than 0.01% (w/w) phenol. In some embodiments the composition comprises substantially no phenol.

Pharmaceutical Compositions

The terms "pharmaceutical composition" and "composition" are used interchangeably herein and refer to pharmaceutical compositions suitable for administration to a subject in need thereof.

In some embodiments the composition comprises 0.01-100 mg/ml semaglutide. In some embodiments the composition comprises 0.1-50 mg/ml, such as 0.5-25 mg/ml or 1-15 mg/ml, semaglutide. In some embodiments the composition comprises 0.1-10 mg/ml, such as 0.5-5 mg/ml or 1-2 mg/ml, semaglutide. In some embodiments the composition comprises 0.01-10 mg/ml, such as 0.01-5 mg/ml, semaglutide. In some embodiments the composition comprises no more than 9 mg/ml, such as no more than 8 mg/ml or no more than 7 mg/ml, semaglutide. In some embodiments the composition comprises no more than 6 mg/ml, such as no more than 5 mg/ml or no more than 4 mg/ml, semaglutide. In some embodiments the composition comprises no more than 3 mg/ml, such as no more than 2 mg/ml or no more than 1 mg/ml, semaglutide. In some embodiments the composition comprises at least 0.01 mg/ml, such as at least 0.02 mg/ml or at least 0.05 mg/ml, semaglutide. In some embodiments the composition comprises 1.34 mg/ml semaglutide.

In some embodiments the composition of the invention has a pH in the range of 3-10, such as pH 6-10 or 6-9. In some embodiments the composition of the invention has a pH in the range of pH 6.5-8.5, such as pH 7.0-7.8.

In some embodiments the composition of the invention comprises one or more pharmaceutically acceptable excipients.

In some embodiments the composition of the invention comprises an isotonic agent, such as propylene glycol. In some embodiments the isotonic agent is propylene glycol or sodium chloride.

In some embodiments the composition of the invention comprises a buffer, such as phosphate buffer, TRIS, citrate, or no buffer. In some embodiments the phosphate buffer is a sodium phosphate buffer, such as disodium hydrogen phosphate.

In some embodiments the composition of the invention comprises no preservative.

The composition of the invention is in the form of a liquid pharmaceutical composition. In some embodiments the liquid pharmaceutical composition is a solution or a suspension. In some embodiments the composition of the invention is in the form of a solution, such as an aqueous solution. In some embodiments the term "aqueous solution" as used herein refers to a solution comprising at least 60% w/w water. In some embodiments the aqueous solution comprises 60-99% w/w water. In some embodiments the aqueous solution comprises at least 75% w/w water, such as at least 80% w/w water or at least 85% w/w water. In some embodiments the aqueous solution comprises at least 90% w/w water, such as at least 92% w/w water or at least 94% w/w water.

Semaglutide

The GLP-1 peptide semaglutide may be prepared as described in WO2006/097537, Example 4. Semaglutide is also known as $N^{6.26}$-{18-[N-(17-carboxyheptadecanoyl)-L-γ-glutamyl]-10-oxo-3,6,12,15-tetraoxa-9,18-diazaoctadecanoyl}-[8-(2-amino-2-propanoic acid),34-L-arginine]human glucagon-like peptide 1(7-37), see WHO Drug Information Vol. 24, No. 1, 2010. In some embodiments semaglutide may be present in the composition in its fully or partly ionised form; for example one or more carboxylic acid groups (—COOH) may be deprotonated into the carboxylate group (—COO⁻) and/or one or more amino groups (—NH$_2$) may be protonated into the —NH$_3$+ group. In some embodiments semaglutide is added to the composition in the form of a salt.

Administration and Kits

The composition of the invention is for parenteral administration. In some embodiments the composition is for subcutaneous administration.

In some embodiments the composition of the invention is for administration once weekly. In some embodiments the composition of the invention is for administration once daily, once every second or once every third day.

In some embodiments the invention relates to a kit comprising the pharmaceutical composition as defined herein and instructions for use. In some embodiments the instructions for use comprise the package insert of a drug.

In some embodiments the invention relates to a kit comprising the pharmaceutical composition as defined herein and an injection device. In some embodiments the injection device is selected from the group consisting of a durable pen and a prefilled pen. Examples of durable pens are NovoPen® 4 or NovoPen® 5 (both from Novo Nordisk A/S, Denmark). An example of a prefilled pen is FlexPen® (Novo Nordisk A/S, Denmark).

Indications

In some embodiments the compositions of the invention are for use in medicine. In some embodiments the composition of the invention may be used for the following medical treatments:

(i) prevention and/or treatment of all forms of diabetes, such as hyperglycaemia, type 2 diabetes, impaired glucose tolerance, type 1 diabetes, non-insulin dependent diabetes, MODY (maturity onset diabetes of the young), gestational diabetes, and/or for reduction of HbA1c;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying.

In some embodiments the indication is (i). In some embodiments the indication is (ii). In a still further particular aspect the indication is (iii). In some embodiments the indication is type 2 diabetes and/or obesity.

In some embodiments the method or use comprises prevention, treatment, reduction and/or induction in one or more diseases or conditions defined herein. In some embodiments the indication is (i) and (iii). In some embodiments the indication is (ii) and (iii). In some embodiments the invention comprises administration of an effective amount of a GLP-1 peptide. In some embodiments the invention relates to administration of an effective amount of a GLP-1 peptide.

Generally, all subjects suffering from obesity are also considered to be suffering from overweight. In some embodiments the invention relates to a method for treatment or prevention of obesity. In some embodiments the invention relates to use of the composition for treatment or prevention of obesity. In some embodiments the subject suffering from obesity is human, such as an adult human or a paediatric human (including infants, children, and adolescents). Body mass index (BMI) is a measure of body fat based on height and weight. The formula for calculation is BMI=weight in kilograms/height in meters². A human subject suffering from obesity may have a BMI of ≥30; this subject may also be referred to as obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity. In some embodiments the invention relates to use of the composition for treatment or prevention of overweight, optionally in the presence of at least one weight-related comorbidity. In some embodiments the subject suffering from overweight is human, such as an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

In some embodiments the invention relates to a method for reduction of body weight. In some embodiments the invention relates to use of the composition for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

In some embodiments, as used herein, specific values given in relation to numbers or intervals may be understood as the specific value or as about the specific value (e.g. plus or minus 10 percent of the specific value).

Embodiments of the Invention

The following are non-limiting embodiments of the invention:
1. A liquid pharmaceutical composition comprising semaglutide and no more than 0.01% (w/w) phenol.
2. A liquid pharmaceutical composition comprising semaglutide and substantially no phenol.
3. The composition according to claim 1 or 2, wherein said composition does not comprise phenol.
4. The composition according to any one of the preceding claims, wherein said composition is an aqueous solution comprising at least 60% w/w water, such as at least 70% w/w water or at least 80% w/w water.
5. The composition according to any one of the preceding claims, wherein the concentration of semaglutide is 0.5-10 mg/ml of said composition.
6. The composition according to any one of the preceding claims, wherein said semaglutide is in the form of a pharmaceutically acceptable salt.
7. The composition according to any one of the preceding claims, wherein said composition comprises one or more pharmaceutically acceptable excipients.
8. The composition according to any one of the preceding claims, wherein said composition comprises one or more agents for adjusting pH, such as HCl, NaOH, or acetate.
9. The composition according to any one of the preceding claims, wherein said composition comprises a buffer and/or an isotonic agent.
10. The composition according to any one of the preceding claims, wherein said buffer is present in a concentration of 0.01-50 mM of said composition.
11. The composition according to any one of the preceding claims, wherein said buffer is a phosphate buffer.
12. The composition according to any one of the preceding claims, wherein said phosphate buffer is selected from the group consisting of sodium dihydrogen phosphate, disodium hydrogen phosphate, and sodium phosphate.
13. The composition according to any one of the preceding claims, wherein said isotonic agent is present in a concentration from 8 mg/ml to 50 mg/ml, such as 14 mg/ml to 30 mg/ml, of said composition.
14. The composition according to any one of the preceding claims, wherein said isotonic is propylene glycol.
15. The composition according to any one of the preceding claims, wherein said composition comprises no preservative.
16. The composition according to any one of the preceding claims, wherein said composition has a pH in the range of 6.0-10.0.
17. The composition according to any one of the preceding claims, wherein said composition is for parenteral administration.
18. The composition according to any one of the preceding claims, wherein said composition is for subcutaneous administration.
19. A kit comprising the pharmaceutical composition as defined in any one of the preceding claims and instructions for use.
20. A kit comprising the pharmaceutical composition as defined in any one of the preceding claims and an injection device for administration of said composition to a subject, wherein said injection device is selected from the group consisting of a durable pen and a prefilled pen.
21. A pharmaceutical composition as defined in any one of the preceding claims for use in medicine.
22. The pharmaceutical composition for use as defined in any one of the preceding claims for use in the treatment of diabetes or obesity.
23. A method for the prevention or treatment of diabetes or obesity, wherein the pharmaceutical composition as defined in any one of the preceding claims is administered to a subject in need thereof.

EXAMPLES

General Methods and Characterisation
Preparation of Semaglutide Compositions:

Unless otherwise noted, compositions of semaglutide were prepared by dissolving buffer (e.g. disodiumhydrogenphosphate dihydrate), isotonic agent (e.g. propylene glycol) and optionally preservative (phenol) in water. Semaglutide was dissolved therein, pH was adjusted to 7.4 using sodium hydroxide and/or hydrochloric acid, and the composition was finally sterilised by filtration through a 0.22 μm sterile filter.

Preparation of Liraglutide Compositions:

Unless otherwise noted, compositions of liraglutide were prepared from Solution 1 and Solution 2: Solution 1 was prepared by dissolving buffer (disodiumhydrogenphosphate dihydrate), isotonic agent (mannitol), and optionally preservative (phenol) in water. Solution 2 was prepared by dissolving liraglutide while stirring slowly. Solution 1 and Solution 2 were mixed, pH was adjusted to 8.15 using sodium hydroxide and/or hydrochloric acid, and the composition was finally sterilised by filtration through a 0.22 μm sterile filter.

Assay (I): Determination of High Molecular Weight Proteins (HMWP) Content of Semaglutide Compositions Determination of HMWP content was performed using size exclusion chromatography (SE-HPLC) using a Waters Insulin HMWP column with a mobile phase of sodium chloride, sodium phosphate, phosphoric acid and isopropanol, isocratic elution and detection at 280 nm. Content of HMWP is given in % as the combined area of chromatographic peaks eluting earlier than the semaglutide monomer peak (i.e. HMWP peaks), relative to the total area of HMWP and semaglutide monomer peaks.

Assay (II): Physical Stability of Semaglutide Compositions Assessed Via ThT

The purpose of this assay is to assess the physical stability of a GLP-1 peptide in aqueous solution.

Low physical stability of a peptide or protein may lead to amyloid fibril formation. Fibrils are structurally well-ordered, filamentous macromolecular structures formed by aggregation of soluble proteins and dominated by beta-sheet structure. Mature fibrils are insoluble and are resistant to degradation. For the sake of drug product quality and patient safety, it is desirable to minimize and control fibrillation events in pharmaceutical compositions of therapeutic peptides and proteins. Protein aggregation, including fibrillation, can be assessed by visual inspection of a sample. Fibrillation can be assessed by the use of Thioflavine T (ThT), a small molecule indicator probe with a high specificity for fibrils. ThT has a distinct fluorescence signature when binding to fibrils compared to ThT in solution [Naiki et al. (1989) Anal. Biochem. 177, 244-249; LeVine (1999) Methods. Enzymol. 309, 274-284].

Formation of a partially folded intermediate of the peptide is suggested as a general initiating mechanism for fibrillation. A small amount of these intermediates nucleates to form a template onto which further intermediates may assembly and the fibrillation proceeds. The lag-time corresponds to the interval in which a critical amount of nuclei is generated and the apparent rate constant is the rate with which the fibril itself is formed. The lag-time described in a ThT assay performed on a plate reader is therefore considered indicative of the fibrillation tendency of a peptide composition in solution.

Before performing the assay, ThT was added to the samples from a stock solution in $H_2O$ to a final concentration of 20 μM in samples. Sample aliquots of 200 μl of the composition comprising the GLP-1 peptide were placed in a 96 well microtiter plate (optical 0.4 mL black Thermo Scientific Nunc) with a glass bead (2.8-3.2 mm, Whitehouse Scientific) placed in each well. Usually, eight replica of each sample were placed on the plate. The plate was sealed with sealing tape (Thermo Scientific Nunc).

Incubation at given temperature, shaking and measurement of the ThT fluorescence emission were performed in a BMG FLUOStar Omega or a BMG FLUOStar Optima. The plate was incubated at 40° C. with double orbital shaking at 300 rpm with an amplitude of 2 mm. Fluorescence measurement was performed using excitation through a 450 nm filter and measurement of emission through a 480 nm filter. The plate was measured every 20 minutes for a desired period of time. Between each measurement, the plate was shaken and heated as described.

The threshold value was determined as the highest ThT fluorescence (in relative fluorescence units (RFU)) measured on the plate at time 1 h 13 min, plus 100 RFU. The threshold value was then used to calculate the lag time using the "time to threshold" method in the BMG FLUOstar software.

Assay (III): Determination of Purity of Liraglutide

Determination of purity was performed using high performance liquid chromatography (HPLC) using a Waters XTerra™ MS C18 column with a gradient elution of two mobile phases, where one mobile phase was an aqueous ammonium phosphate buffer (pH 8)/acetonitrile mixture and the other mobile phase was acetonitrile in water. Detection was performed at 215 nm.

Assay (IV): Determination of Sum of Impurities of Semaglutide

Determination of purity of semaglutide is performed using reversed phase high performance liquid chromatography (RP-HPLC) using a Kinetex C18 column with an isocratic elution followed by a gradient elution of two mobile phases, where one mobile phase was an aqueous phosphate buffer/acetonitrile mixture and the other mobile phase was an aqueous acetonitrile/isopropanol mixture. Detection was performed at 210 nm. Purity of semaglutide is given as sum of impurities in % as the combined area of all chromatographic peaks relative to semaglutide monomer peaks.

Example 1: Semaglutide

Compositions comprising semaglutide were tested in this experiment. The tested compositions contained semaglutide (as specified in Table 1), propylene glycol (14 mg/ml), disodiumhydrogenphosphate dihydrate (1.42 mg/ml), and optionally phenol (5.5 mg/ml) (as specified in Table 1), at pH 7.4 in an aqueous solution. These compositions were prepared as described herein in the section General Methods of Preparation. Chemical stability as expressed by HMWP was determined by Assay (I) described herein at start of the experiment and after storage at 25° C., 30° C. or at 37° C. Physical stability as expressed by Thioflavin T (ThT) assay was determined by Assay (II) described herein.

The results are given in Tables 2 and 3. Surprisingly, these results show that physical and chemical stability of semaglutide were improved in compositions without phenol relative to those with phenol. Results shown in Table 3 are an average of 8 samples tested.

TABLE 1

Compositions tested in Example 1

| Composition no. | Description |
|---|---|
| 1 | Semaglutide 1 mg/ml, with phenol |
| 2 | Semaglutide 1 mg/ml, without phenol |
| 3 | Semaglutide 1.34 mg/ml, with phenol |
| 4 | Semaglutide 1.34 mg/ml, without phenol |
| 5 | Semaglutide 0.5 mg/ml, without phenol |
| 6 | Semaglutide 0.5 mg/ml, with phenol |
| 7 | Semaglutide 1.0 mg/ml, without phenol |
| 8 | Semaglutide 1.0 mg/ml, with phenol |
| 9 | Semaglutide 2.0 mg/ml, without phenol |
| 10 | Semaglutide 2.0 mg/ml, with phenol |

TABLE 2

Chemical stability of semaglutide compositions, as expressed by content of high molecular weight proteins (HMWP), following storage at different temperatures. A lower HMWP concentration corresponds to a better chemical stability.

| | HMWP (%) | | | |
|---|---|---|---|---|
| Composition no. | 0 months | 25° C. 6 months | 30° C. 3 months | 37° C. 3 months |
| 1 | 0.1 | 2.0 | 1.9 | 4.1 |
| 2 (no phenol) | 0.1 | 0.3 | 0.3 | 0.5 |
| 3 | 0.1 | 1.9 | 1.8 | 3.9 |
| 4 (no phenol) | 0.1 | 0.3 | 0.4 | 0.6 |

TABLE 3

Physical stability of semaglutide compositions as expressed by Thioflavin T (ThT) assay. A longer lag time corresponds to a better physical stability.

| Composition no. | Lag time (hours) |
|---|---|
| 5 (no phenol) | >117 |
| 6 | 19 |
| 7 (no phenol) | >117 |
| 8 | 35 |
| 9 (no phenol) | >117 |
| 10 | 35 |

Example 2 (Reference): Liraglutide

The results of Example 1 are also surprising in view of the fact that the GLP-1 compound liraglutide—contrary to semaglutide—is less chemically stable in a composition without phenol. These results are shown in Table 5.

The results in Table 5 were obtained as follows: Compositions comprising liraglutide were tested. The tested compositions contained liraglutide (as specified in Table 4), mannitol (36.9 mg/ml), disodium hydrogen phosphate (1.42 mg/ml), and optionally phenol (as specified in Table 4), at pH 7.4 in an aqueous solution. These compositions were prepared as described herein in the section General Methods of Preparation. Chemical stability as expressed by purity was determined by Assay (III) described herein at start of the experiment and after storage at 25° C. or at 37° C.

TABLE 4

Compositions tested in Example 2

| Composition no. | Description |
|---|---|
| 11 | Liraglutide (3 mg/ml), without phenol (pH 7.4) |
| 12 | Liraglutide (3 mg/ml), phenol (0.04 mg/ml) (pH 7.4) |
| 13 | Liraglutide (3 mg/ml), phenol (0.16 mg/ml) (pH 7.4) |
| 14 | Liraglutide (3 mg/ml), phenol (0.8 mg/ml) (pH 7.4) |
| 15 | Liraglutide (3 mg/ml), phenol (2.5 mg/ml) (pH 7.4) |

TABLE 5

Chemical stability, as expressed by purity, of compositions comprising liraglutide following storage at different temperatures. A higher purity corresponds to a better chemical stability.

| Composition no. | Purity (%) | | |
|---|---|---|---|
| | 0 months | 3 months at 25° C. | 3 months at 37° C. |
| 11 (no phenol) | 98 | 88 | 72 |
| 12 | 98 | 93 | 80 |
| 13 | 98 | 94 | 81 |
| 14 | 97 | 95 | 83 |
| 15 | 98 | 95 | 84 |

Example 3: Semaglutide—Additional Experiments

Compositions comprising semaglutide were tested in this experiment. The tested compositions contained semaglutide, isotonic agent (propylene glycol (14 mg/ml) or sodium chloride (6.3 mg/ml)), optionally buffer (disodiumhydrogenphosphate dihydrate (1.42 mg/ml) or trisodiumcitrate dihydrate (2.35 mg/ml)), and optionally phenol (5.5 mg/ml or 0.1 mg/ml), at pH 7.0, 7.4 or 7.8 in an aqueous solution; details of each composition tested is shown in Table 6. The compositions were prepared as described herein in the section General Methods of Preparation. Chemical stability as expressed by HMWP was determined by Assay (I) and as expressed by sum of impurities was determined by Assay (IV) described herein at start of the experiment and after storage at 30° C. Physical stability as expressed by Thioflavin T (ThT) assay was determined by Assay (II) described herein.

The results are given in Table 7 and 8. In line with the results of Example 1, these results show that physical stability and chemical stability of semaglutide were improved in compositions without or with low phenol concentration relative to those with phenol at 5.5 mg/ml. The results show that physical stability and chemical stability of semaglutide were also improved in compositions without phenol comprising either the buffer trisodiumcitrate dihydrate or no buffer or isotonic agent sodium chloride, relative to those with phenol. Chemical and physical stability were improved for compositions with 0.1 mg/ml phenol relative to compositions with 5.5 mg/ml phenol and similar to compositions with no phenol. This was demonstrated for compositions with pH 7.0-7.8 and semaglutide concentration 0.1-10 mg/ml.

TABLE 6

Compositions tested in Example 3

| Comp. No. | Content of composition | | | | |
|---|---|---|---|---|---|
| | Semaglutide (mg/ml) | Phenol (mg/ml) | Buffer | Isotonic agent | pH |
| 1 | 0.5 | 0 | Phos* | PG** | 7.0 |
| 2 | 0.5 | 0.1 | Phos | PG | 7.0 |
| 3 | 0.5 | 5.5 | Phos | PG | 7.0 |
| 4 | 0.5 | 0 | Phos | PG | 7.4 |
| 5 | 0.5 | 0.1 | Phos | PG | 7.4 |
| 6 | 0.5 | 5.5 | Phos | PG | 7.4 |
| 7 | 0.5 | 0 | Phos | PG | 7.8 |
| 8 | 0.5 | 0.1 | Phos | PG | 7.8 |
| 9 | 0.5 | 5.5 | Phos | PG | 7.8 |
| 10 | 10 | 0 | Phos | PG | 7.0 |
| 11 | 10 | 0.1 | Phos | PG | 7.0 |
| 12 | 10 | 5.5 | Phos | PG | 7.0 |
| 13 | 10 | 0 | Phos | PG | 7.4 |
| 14 | 10 | 0.1 | Phos | PG | 7.4 |
| 15 | 10 | 5.5 | Phos | PG | 7.4 |
| 16 | 10 | 0 | Phos | PG | 7.8 |
| 17 | 10 | 0.1 | Phos | PG | 7.8 |
| 18 | 10 | 5.5 | Phos | PG | 7.8 |
| 19 | 0.1 | 0 | Phos | PG | 7.4 |
| 20 | 0.1 | 5.5 | Phos | PG | 7.4 |
| 21 | 0.5 | 0 | Phos | Citrate*** | 7.4 |
| 22 | 0.5 | 5.5 | Phos | Citrate | 7.4 |
| 23 | 0.5 | 0 | Phos | None# | 7.4 |
| 24 | 0.5 | 5.5 | Phos | None | 7.4 |
| 25 | 0.5 | 0 | NaCl## | PG | 7.4 |
| 26 | 0.5 | 5.5 | NaCl | PG | 7.4 |

*Phos: Disodiumhydrogenphosphate dihydrate, 1.42 mg/ml.
**PG: Propylene glycol, 14 mg/ml.
***Citrate: Trisodiumcitrate dihydrate, 2.35 mg/ml.
None: No pharmaceutical excipeints added in the form of a buffer.
NaCl: Sodium chloride, 6.3 mg/ml.

TABLE 7

Chemical stability of semaglutide compositions, as expressed by content of high molecular weight proteins (HMWP) and sum of impurities, following storage at 30° C. temperature. A lower HMWP concentration and sum of impurities concentration corresponds to a better chemical stability.

| Composition No. | DS (mg/ml) | Phenol (mg/ml) | HMWP (%) 0 months | HMWP (%) 30° C. 3 months | Sum of impurities (%) 0 months | Sum of impurities (%) 30° C. 3 months |
|---|---|---|---|---|---|---|
| 1 (pH 7.0) | 0.5 | 0 | 0.1 | 0.3 | 3.1 | 7.0 |
| 2 (pH 7.0) | 0.5 | 0.1 | 0.1 | 0.3 | 3.2 | 7.2 |
| 3 (pH 7.0) | 0.5 | 5.5 | 0.1 | 1.4 | 3.2 | 7.8 |
| 4 (pH 7.4) | 0.5 | 0 | 0.1 | 0.3 | 3.1 | 6.7 |
| 5 (pH 7.4) | 0.5 | 0.1 | 0.1 | 0.3 | 3.2 | 6.6 |
| 6 (pH 7.4) | 0.5 | 5.5 | 0.1 | 2.4 | 3.2 | 8.4 |
| 7 (pH 7.8) | 0.5 | 0 | 0.1 | 0.2 | 3.1 | 6.5 |
| 8 (pH 7.8) | 0.5 | 0.1 | 0.1 | 0.3 | 3.2 | 6.6 |
| 9 (pH 7.8) | 0.5 | 5.5 | 0.1 | 4.8 | 3.1 | 10.6 |
| 10 (pH 7.0) | 10 | 0 | 0.1 | 1.4 | 3.1 | 8.4 |
| 11 (pH 7.0) | 10 | 0.1 | 0.1 | 0.7 | 3.1 | 7.7 |
| 12 (pH 7.0) | 10 | 5.5 | 0.1 | N/A[1] | 3.0 | N/A[1] |
| 13 (pH 7.4) | 10 | 0 | 0.1 | 0.9 | 3.1 | 7.8 |
| 14 (pH 7.4) | 10 | 0.1 | 0.1 | 0.7 | 3.1 | 6.9 |
| 15 (pH 7.4) | 10 | 5.5 | 0.1 | 0.8 | 3.0 | 6.9 |
| 16 (pH 7.8) | 10 | 0 | 0.1 | 0.9 | 3.0 | 6.6 |
| 17 (pH 7.8) | 10 | 0.1 | 0.1 | 0.6 | 3.1 | 6.8 |
| 18 (pH 7.8) | 10 | 5.5 | 0.1 | 1.0 | 3.1 | 6.9 |
| 19 (low DS) | 0.1 | 0 | 0.1 | 0.2 | 3.5 | 7.7 |
| 20 (low DS) | 0.1 | 5.5 | 0.1 | 4.7 | 3.7 | 11.4 |
| 21 (citrate) | 0.5 | 0 | 0.1 | 0.2 | 3.1 | 6.2 |
| 22 (citrate) | 0.5 | 5.5 | 0.1 | 2.2 | 3.2 | 7.7 |
| 23 (no buffer) | 0.5 | 0 | 0.1 | 0.2 | 3.2 | 6.9 |
| 24 (no buffer) | 0.5 | 5.5 | 0.1 | 2.3 | 3.2 | 9.3 |
| 25 (NaCl) | 0.5 | 0 | 0.1 | 0.3 | 3.1 | 6.4 |
| 26 (NaCl) | 0.5 | 5.5 | 0.1 | 3.4 | 3.2 | 8.9 |

DS: Semaglutide.
[1]Not physically stable >1 month at 30° C.

TABLE 8

Physical stability of semaglutide compositions as expressed by Thioflavin T (ThT) assay. A longer lag time corresponds to a better physical stability.

| Composition No. | Semaglutide (mg/ml) | Phenol (mg/ml) | Lag time (hours) |
|---|---|---|---|
| 1 (pH 7.0) | 0.5 | 0 | 42 |
| 2 (pH 7.0) | 0.5 | 0.1 | 63 |
| 3 (pH 7.0) | 0.5 | 5.5 | 5 |
| 4 (pH 7.4) | 0.5 | 0 | >117 |
| 5 (pH 7.4) | 0.5 | 0.1 | >117 |
| 6 (pH 7.4) | 0.5 | 5.5 | 87 |
| 7 (pH 7.8) | 0.5 | 0 | >117 |
| 8 (pH 7.8) | 0.5 | 0.1 | >117 |
| 9 (pH 7.8) | 0.5 | 5.5 | >117 |
| 10 (pH 7.0) | 10 | 0 | 117 |
| 11 (pH 7.0) | 10 | 0.1 | >117 |
| 12 (pH 7.0) | 10 | 5.5 | 25 |
| 13 (pH 7.4) | 10 | 0 | >117 |
| 14 (pH 7.4) | 10 | 0.1 | >117 |
| 15 (pH 7.4) | 10 | 5.5 | >117 |
| 16 (pH 7.8) | 10 | 0 | >117 |
| 17 (pH 7.8) | 10 | 0.1 | >117 |
| 18 (pH 7.8) | 10 | 5.5 | >117 |
| 19 (low DS) | 0.1 | 0 | >117 |
| 20 (low DS) | 0.1 | 5.5 | >117 |
| 21 (citrate) | 0.5 | 0 | >117 |
| 22 (citrate) | 0.5 | 5.5 | >117 |
| 23 (no buffer) | 0.5 | 0 | >117 |
| 24 (no buffer) | 0.5 | 5.5 | 4 |
| 25 (NaCl) | 0.5 | 0 | >117 |
| 26 (NaCl) | 0.5 | 5.5 | 8 |

Results are an average of 8 samples tested.
DS: Semaglutide.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A liquid pharmaceutical composition comprising semaglutide and phenol, wherein said composition
   (a) is for parenteral administration;
   (b) is an aqueous solution comprising at least 60% w/w) water; or
   (c) further comprises one or more pharmaceutically acceptable excipients selected from the group consisting of a buffer or an isotonic agent;
   wherein the semaglutide is in the range of 0.5 mg/ml-5.0 mg/ml;
   wherein the phenol is no more than 0.1 mg/ml; and
   wherein the pH of the composition is in between 7.0 and 7.8.

2. The composition according to claim 1, wherein said composition comprises one or more pharmaceutically acceptable excipients.

3. The composition according to claim 2, wherein said one or more pharmaceutically acceptable excipients are selected from the group consisting of a buffer or an isotonic agent.

4. The composition according to claim 3, wherein said buffer is a phosphate buffer.

5. The composition according to claim 3, wherein said isotonic agent is selected from propylene glycol or sodium chloride.

6. The composition according to claim 1, wherein said composition comprises no preservative.

7. The composition according to claim 1, wherein said composition has a pH in the range of 7.0-7.4.

8. The composition according to claim 1, wherein said parenteral administration is subcutaneous administration.

9. The composition according to claim 1, wherein said composition comprises 0.5 mg/ml-5.0 mg/ml semaglutide, propylene glycol and 1.42 mg/ml disodiumhydrogenphosphate dihydrate.

10. The composition according to claim 1, wherein said composition comprises 0.5 mg/ml-5.0 mg/ml semaglutide, sodium chloride and 1.42 mg/ml disodiumhydrogenphosphate dihydrate.

11. A kit comprising a liquid pharmaceutical composition of claim 1 and instructions for use.

12. A kit comprising a liquid pharmaceutical composition of claim 1 and an injection device for administration of said composition to a subject, wherein said injection device is selected from the group consisting of a durable pen and a prefilled pen.

13. A method of treating diabetes comprising administering to a subject in need of such treatment a therapeutically effective amount of a composition according to claim 1.

14. A method of treating obesity comprising administering to a subject in need of such treatment a therapeutically effective amount of a composition according to claim 1.

\* \* \* \* \*